(12) United States Patent
Donohoe et al.

(10) Patent No.: US 6,719,769 B2
(45) Date of Patent: Apr. 13, 2004

(54) INTEGRATED ANASTOMOSIS TOOL WITH GRAFT VESSEL ATTACHMENT DEVICE AND CUTTING DEVICE

(75) Inventors: Brendan M. Donohoe, San Francisco, CA (US); Jaime Vargas, Menlo Park, CA (US); Stephen A. Yencho, Menlo Park, CA (US); James T. Nielsen, San Francisco, CA (US); Theodore M. Bender, San Francisco, CA (US); Michael Hendricksen, Redwood City, CA (US); Scott C. Anderson, Sunnyvale, CA (US)

(73) Assignee: Cardica, Inc., Redwood City, CA (US)

( * ) Notice: Subject to any disclaimer, the term of this patent is extended or adjusted under 35 U.S.C. 154(b) by 286 days.

(21) Appl. No.: 10/001,962

(22) Filed: Dec. 5, 2001

(65) Prior Publication Data

US 2002/0082626 A1 Jun. 27, 2002

Related U.S. Application Data

(63) Continuation-in-part of application No. 09/440,263, filed on Nov. 15, 1999, now Pat. No. 6,371,964.

(51) Int. Cl.[7] .............................................. A61B 17/04
(52) U.S. Cl. ...................................................... 606/153
(58) Field of Search ......................................... 606/153

(56) References Cited

U.S. PATENT DOCUMENTS

| 2,370,776 A | 3/1945 | Carlson |
| 3,254,650 A | 6/1966 | Collito |
| 3,254,651 A | 6/1966 | Collito |
| 3,519,187 A | 7/1970 | Kapitanov et al. |
| 3,774,615 A | 11/1973 | Lim et al. |
| 4,118,806 A | 10/1978 | Porier et al. |
| 4,214,587 A | 7/1980 | Sakura, Jr. |
| 4,217,664 A | 8/1980 | Faso |
| 4,350,160 A | 9/1982 | Kolesov et al. |
| 4,352,358 A | 10/1982 | Angelchik |
| 4,366,819 A | 1/1983 | Kaster |
| 4,368,736 A | 1/1983 | Kaster |
| 4,503,568 A | 3/1985 | Madras |
| 4,523,592 A | 6/1985 | Daniel |
| 4,534,761 A | 8/1985 | Raible |

(List continued on next page.)

FOREIGN PATENT DOCUMENTS

| DE | 29713335.7 | 11/1997 |
| DE | 19732234 | 1/1999 |
| EP | 0 701 800 | 3/1996 |
| EP | 0 885 595 | 12/1998 |
| EP | 0 938 870 | 9/1999 |
| EP | 0 820 724 | 1/2000 |
| EP | 0 820 725 | 1/2000 |
| EP | 0 913 125 | 7/2000 |
| EP | 0 990 420 | 12/2000 |
| FR | 2316910 | 4/1977 |

(List continued on next page.)

Primary Examiner—Gary Jackson
(74) Attorney, Agent, or Firm—Brian A. Schar; Cindy A. Lynch

(57) ABSTRACT

An integrated anastomosis tool both creates an opening in a side wall of a target blood vessel and performs an anastomosis procedure to connect a graft vessel to a side of the target blood vessel with a single integrated tool. The integrated anastomosis tool includes a cutting device, a graft vessel attachment device, an introducer, and a tool body. In each of the embodiments of the anastomosis tool, the advancement paths of a cutting device and a graft vessel attachment device cross, intersect, or align so that both the cutting device and the graft vessel attachment device can be operated by a single tool at the same intended anastomosis site in a sequential manner. The anastomosis procedure can be performed on a pressurized vessel since there is no need to interchange tools during the procedure.

29 Claims, 11 Drawing Sheets

U.S. PATENT DOCUMENTS

| | | |
|---|---|---|
| 4,553,542 A | 11/1985 | Schenck et al. |
| 4,577,631 A | 3/1986 | Kreamer |
| 4,589,416 A | 5/1986 | Green |
| 4,593,693 A | 6/1986 | Schenck |
| 4,603,693 A | 8/1986 | Conta et al. |
| 4,607,637 A | 8/1986 | Berggren et al. |
| 4,624,255 A | 11/1986 | Schenck et al. |
| 4,624,257 A | 11/1986 | Berggren et al. |
| 4,657,019 A | 4/1987 | Walsh et al. |
| 4,665,906 A | 5/1987 | Jervis |
| 4,721,109 A | 1/1988 | Healey |
| 4,747,407 A | 5/1988 | Liu et al. |
| 4,752,024 A | 6/1988 | Green et al. |
| 4,773,420 A | 9/1988 | Green |
| 4,861,330 A | 8/1989 | Voss |
| 4,875,815 A | 10/1989 | Phillips, II |
| 4,883,453 A | 11/1989 | Berry et al. |
| 4,892,098 A | 1/1990 | Sauer |
| 4,907,591 A | 3/1990 | Vasconcellos et al. |
| 4,917,087 A | 4/1990 | Walsh et al. |
| 4,917,090 A | 4/1990 | Berggren et al. |
| 4,917,091 A | 4/1990 | Berggren et al. |
| 4,930,674 A | 6/1990 | Barak |
| 5,005,749 A | 4/1991 | Aranyi |
| 5,015,238 A | 5/1991 | Solomon et al. |
| 5,062,842 A | 11/1991 | Tiffany |
| 5,089,006 A | 2/1992 | Stiles |
| 5,104,025 A | 4/1992 | Main et al. |
| 5,119,983 A | 6/1992 | Green et al. |
| 5,129,913 A | 7/1992 | Ruppert |
| 5,156,613 A | 10/1992 | Sawyer |
| 5,156,619 A | 10/1992 | Ehrenfeld |
| 5,171,262 A | 12/1992 | MacGregor |
| 5,178,634 A | 1/1993 | Ramos Martinez |
| 5,187,796 A | 2/1993 | Wang et al. |
| 5,192,289 A | 3/1993 | Jessen |
| 5,193,731 A | 3/1993 | Aranyi |
| 5,205,459 A | 4/1993 | Brinkerhoff et al. |
| 5,211,683 A | 5/1993 | Maginot |
| 5,217,474 A | 6/1993 | Zacca et al. |
| 5,221,281 A | 6/1993 | Klicek |
| 5,222,963 A | 6/1993 | Brinkerhoff et al. |
| 5,234,447 A | 8/1993 | Kaster et al. |
| 5,250,058 A | 10/1993 | Miller et al. |
| 5,250,060 A | 10/1993 | Carbo et al. |
| 5,271,544 A | 12/1993 | Fox et al. |
| 5,275,322 A | 1/1994 | Brinkerhoff et al. |
| 5,285,945 A | 2/1994 | Brinkerhoff et al. |
| 5,290,298 A | 3/1994 | Rebuffat et al. |
| 5,292,053 A | 3/1994 | Bilotti et al. |
| 5,304,220 A | 4/1994 | Maginot |
| 5,314,435 A | 5/1994 | Green et al. |
| 5,314,468 A | 5/1994 | Martinez |
| 5,326,205 A | 7/1994 | Anspach, Jr. et al. |
| 5,333,773 A | 8/1994 | Main et al. |
| 5,336,233 A | 8/1994 | Chen |
| 5,350,104 A | 9/1994 | Main et al. |
| 5,354,302 A | 10/1994 | Ko |
| 5,364,389 A | 11/1994 | Anderson |
| 5,366,462 A | 11/1994 | Kaster et al. |
| 5,392,979 A | 2/1995 | Green et al. |
| 5,395,030 A | 3/1995 | Kuramoto et al. |
| 5,395,311 A | 3/1995 | Andrews |
| 5,401,131 A | 3/1995 | Yoshino |
| 5,443,497 A | 8/1995 | Venbrux |
| 5,447,514 A | 9/1995 | Gerry et al. |
| 5,454,825 A | 10/1995 | Van Leeuwen |
| 5,456,712 A | 10/1995 | Maginot |
| 5,456,714 A | 10/1995 | Owen |
| 5,464,449 A | 11/1995 | Ryan et al. |
| 5,465,895 A | 11/1995 | Knodel et al. |
| 5,478,354 A | 12/1995 | Tovey et al. |
| 5,503,635 A | 4/1996 | Sauer et al. |
| 5,515,478 A | 5/1996 | Wang |
| 5,522,834 A | 6/1996 | Fonger et al. |
| 5,524,180 A | 6/1996 | Wang et al. |
| 5,533,661 A | 7/1996 | Main et al. |
| 5,540,677 A | 7/1996 | Sinofsky |
| 5,553,198 A | 9/1996 | Wang et al. |
| 5,556,405 A | 9/1996 | Lary |
| 5,558,667 A | 9/1996 | Yarborough et al. |
| 5,571,167 A | 11/1996 | Maginot |
| 5,643,340 A | 7/1997 | Nunokawa |
| 5,645,520 A | 7/1997 | Nakamura et al. |
| 5,657,429 A | 8/1997 | Wang et al. |
| 5,669,918 A | 9/1997 | Balazs et al. |
| 5,669,934 A | 9/1997 | Sawyer |
| 5,676,670 A | 10/1997 | Kim |
| 5,693,088 A | 12/1997 | Lazarus |
| 5,695,504 A | 12/1997 | Gifford, III et al. |
| 5,702,412 A | 12/1997 | Popov et al. |
| 5,707,362 A | 1/1998 | Yoon |
| 5,707,380 A | 1/1998 | Hinchliffe et al. |
| 5,709,335 A | 1/1998 | Heck |
| 5,709,693 A | 1/1998 | Taylor |
| 5,725,544 A | 3/1998 | Rygaard |
| 5,725,553 A | 3/1998 | Moenning |
| 5,732,872 A | 3/1998 | Bolduc et al. |
| 5,754,741 A | 5/1998 | Wang et al. |
| 5,755,778 A | 5/1998 | Kleshinski |
| 5,762,458 A | 6/1998 | Wang et al. |
| 5,779,718 A | 7/1998 | Green et al. |
| 5,792,135 A | 8/1998 | Madhani et al. |
| 5,797,900 A | 8/1998 | Madhani et al. |
| 5,797,920 A | 8/1998 | Kim |
| 5,799,661 A | 9/1998 | Boyd et al. |
| 5,799,857 A | 9/1998 | Robertson et al. |
| 5,807,377 A | 9/1998 | Madhani et al. |
| 5,814,073 A | 9/1998 | Bonutti |
| 5,815,640 A | 9/1998 | Wang et al. |
| 5,817,113 A | 10/1998 | Gifford, III et al. |
| 5,827,316 A | 10/1998 | Young et al. |
| 5,833,698 A | 11/1998 | Hinchliffe et al. |
| 5,841,950 A | 11/1998 | Wang et al. |
| 5,855,583 A | 1/1999 | Wang et al. |
| 5,868,763 A | 2/1999 | Spence et al. |
| 5,875,782 A | 3/1999 | Ferrari et al. |
| 5,878,193 A | 3/1999 | Wang et al. |
| 5,879,371 A | 3/1999 | Gardiner et al. |
| 5,881,943 A | 3/1999 | Heck et al. |
| 5,893,369 A | 4/1999 | Lemole |
| 5,904,697 A | 5/1999 | Gifford, III et al. |
| 5,907,664 A | 5/1999 | Wang et al. |
| 5,911,036 A | 6/1999 | Wright et al. |
| 5,915,616 A | 6/1999 | Viola et al. |
| 5,921,995 A | 7/1999 | Kleshinski |
| 5,944,730 A | 8/1999 | Nobles et al. |
| 5,947,363 A | 9/1999 | Bolduc et al. |
| 5,957,363 A | 9/1999 | Heck |
| 5,968,089 A | 10/1999 | Krajicek |
| 5,976,159 A | 11/1999 | Bolduc et al. |
| 6,001,124 A | 12/1999 | Bachinski |
| 6,007,544 A | 12/1999 | Kim |
| 6,013,190 A | 1/2000 | Berg et al. |
| 6,015,416 A | 1/2000 | Stefanchik et al. |
| 6,022,367 A | 2/2000 | Sherts |
| 6,024,748 A | 2/2000 | Manzo et al. |
| 6,030,370 A | 2/2000 | Kupka et al. |
| 6,030,395 A | 2/2000 | Nash et al. |
| 6,036,699 A | 3/2000 | Andreas et al. |
| 6,036,700 A | 3/2000 | Stefanchik et al. |

| | | | | | |
|---|---|---|---|---|---|
| 6,036,702 A | 3/2000 | Bachinski et al. | WO | 98/30153 | 7/1998 |
| 6,036,703 A | 3/2000 | Evans et al. | WO | 98/37814 | 9/1998 |
| 6,036,704 A | 3/2000 | Yoon | WO | 98/40036 | 9/1998 |
| 6,036,705 A | 3/2000 | Nash et al. | WO | 98/42262 | 10/1998 |
| 6,050,472 A | 4/2000 | Shibata | WO | 98/47430 | 10/1998 |
| 6,053,390 A | 4/2000 | Green et al. | WO | 98/55027 | 12/1998 |
| 6,056,762 A | 5/2000 | Nash et al. | WO | 99/08603 | 2/1999 |
| 6,066,144 A | 5/2000 | Wolf et al. | WO | 99/11178 | 3/1999 |
| 6,066,148 A | 5/2000 | Rygaard | WO | 99/17665 | 4/1999 |
| 6,068,637 A | 5/2000 | Popov et al. | WO | 99/18887 | 4/1999 |
| 6,074,416 A | 6/2000 | Berg et al. | WO | 99/21491 | 5/1999 |
| 6,080,167 A | 6/2000 | Lyell | WO | 99/37218 | 7/1999 |
| 6,080,173 A | 6/2000 | Williamson, IV et al. | WO | 99/38441 | 8/1999 |
| 6,083,234 A | 7/2000 | Nicholas et al. | WO | 99/38454 | 8/1999 |
| 6,110,188 A | 8/2000 | Narciso, Jr. | WO | 99/40851 | 8/1999 |
| 6,113,612 A | 9/2000 | Swanson et al. | WO | 99/40868 | 8/1999 |
| 6,117,148 A | 9/2000 | Ravo et al. | WO | 99/45848 | 9/1999 |
| 6,120,432 A | 9/2000 | Sullivan et al. | WO | 99/52481 | 10/1999 |
| 6,146,393 A | 11/2000 | Wakabayashi | WO | 99/62415 | 10/1999 |
| 6,149,681 A | 11/2000 | Houser et al. | WO | 99/62406 | 12/1999 |
| 6,152,937 A | 11/2000 | Peterson et al. | WO | 99/62409 | 12/1999 |
| 6,152,945 A | 11/2000 | Bachinski et al. | WO | 99/63910 | 12/1999 |
| 6,165,185 A | 12/2000 | Shennib et al. | WO | 99/65409 | 12/1999 |
| 6,167,889 B1 | 1/2001 | Benetti | WO | 00/09040 | 2/2000 |
| 6,171,319 B1 | 1/2001 | Nobles et al. | WO | 00/10486 | 3/2000 |
| 6,171,321 B1 | 1/2001 | Gifford, III et al. | WO | 00/12013 | 3/2000 |
| 6,176,413 B1 | 1/2001 | Heck et al. | WO | 00/15144 | 3/2000 |
| 6,176,864 B1 | 1/2001 | Chapman | WO | 00/15146 | 3/2000 |
| 6,186,942 B1 | 2/2001 | Sullivan et al. | WO | 00/15147 | 3/2000 |
| 6,187,019 B1 | 2/2001 | Stefanchik et al. | WO | 00/15148 | 3/2000 |
| 6,187,020 B1 | 2/2001 | Zegdi et al. | WO | 00/15149 | 3/2000 |
| 6,190,396 B1 | 2/2001 | Whitin et al. | WO | 00/27310 | 5/2000 |
| 6,190,397 B1 | 2/2001 | Spence et al. | WO | 00/27311 | 5/2000 |
| 6,190,590 B1 | 2/2001 | Randall et al. | WO | 00/27312 | 5/2000 |
| 6,193,129 B1 | 2/2001 | Bittner et al. | WO | 00/27313 | 5/2000 |
| 6,193,734 B1 | 2/2001 | Bolduc et al. | WO | 00/33745 | 6/2000 |
| 6,206,912 B1 | 3/2001 | Goldsteen et al. | WO | 00/41633 | 7/2000 |
| 6,206,913 B1 | 3/2001 | Yencho et al. | WO | 00/53104 | 9/2000 |
| 6,235,054 B1 | 5/2001 | Berg et al. | WO | 00/56223 | 9/2000 |
| 6,485,496 B1 | 11/2002 | Suyker et al. ............... 606/153 | WO | 00/56226 | 9/2000 |
| 2003/0065342 A1 | 4/2003 | Nobis ......................... 606/153 | WO | 00/56227 | 9/2000 |
| | | | WO | 00/56228 | 9/2000 |

FOREIGN PATENT DOCUMENTS

| | | | | | |
|---|---|---|---|---|---|
| | | | WO | 00/59380 | 10/2000 |
| WO | 92/08513 | 5/1992 | WO | 00/66007 | 11/2000 |
| WO | 0/517252 | 12/1992 | WO | 00/66009 | 11/2000 |
| WO | 96/25886 | 8/1996 | WO | 00/69343 | 11/2000 |
| WO | 97/25002 | 7/1997 | WO | 00/69346 | 11/2000 |
| WO | 97/27898 | 8/1997 | WO | 00/69349 | 11/2000 |
| WO | 97/31575 | 9/1997 | WO | 00/69364 | 11/2000 |
| WO | 97/47261 | 12/1997 | WO | 00/72764 | 12/2000 |
| WO | 98/07399 | 2/1998 | WO | 00/74579 | 12/2000 |
| WO | 98/19608 | 5/1998 | WO | 00/76405 | 12/2000 |
| WO | 98/19618 | 5/1998 | WO | 01/08601 | 2/2001 |
| WO | 98/19625 | 5/1998 | WO | 01/12074 | 2/2001 |
| WO | 98/19629 | 5/1998 | WO | 01/15607 | 3/2001 |
| WO | 98/19630 | 5/1998 | WO | 01/17440 | 3/2001 |
| WO | 98/19631 | 5/1998 | WO | 01/19257 | 3/2001 |
| WO | 98/19632 | 5/1998 | WO | 01/19259 | 3/2001 |
| WO | 98/19634 | 5/1998 | WO | 01/19284 | 3/2001 |
| WO | 98/19636 | 5/1998 | WO | 01/34037 | 5/2001 |

INTEGRATED ANASTOMOSIS TOOL WITH GRAFT VESSEL ATTACHMENT DEVICE AND CUTTING DEVICE

CROSS REFERENCE TO RELATED APPLICATIONS

This application is a Continuation-in-part of U.S. patent application Ser. No. 09/440,263 filed on Nov. 15, 1999 now U.S. Pat. No. 6,371,964, which is incorporated herein by reference in its entirety.

1. Field of the Invention

The invention relates to an integrated anastomosis tool with a graft vessel attachment device and a cutting device, and more particularly, the invention relates to a system and method for both creating an opening in a target blood vessel and performing an anastomosis procedure with a single integrated tool.

2. Description of the Related Art

Vascular anastomosis is a procedure by which two blood vessels within a patient are surgically joined together. Vascular anastomosis is performed during treatment of a variety of conditions including coronary artery disease, diseases of the great and peripheral vessels, organ transplantation, and trauma. In coronary artery disease (CAD) an occlusion or stenosis in a coronary artery interferes with blood flow to the heart muscle. Treatment of CAD involves the grafting of a vessel in the form of a prosthesis or harvested artery or vein to reroute blood flow around the occlusion and restore adequate blood flow to the heart muscle. This treatment is known as coronary artery bypass grafting (CABG).

In conventional CABG, a large incision is made in the chest and the sternum is sawed in half to allow access to the heart. In addition, a heart lung machine is used to circulate the blood so that the heart can be stopped and the anastomosis can be performed. During this procedure, the aorta is clamped which can lead to trauma of the aortic tissue and/or dislodge plaque emboli, both of which increase the likelihood of neurological complications.

In order to minimize the trauma to the patient induced by conventional CABG, less invasive techniques have been developed in which the surgery is performed through small incisions or keyhole openings in the chest with the aid of visualizing scopes. Less invasive CABG can be performed on a beating or stopped heart and thus may avoid the need for cardiopulmonary bypass.

In both conventional and less invasive CABG procedures, the surgeon has to suture one end of the graft vessel to the coronary artery and the other end of the graft vessel to a blood supplying vein or artery. The suturing process is a time consuming and difficult procedure requiring a high level of surgical skill. In order to perform the suturing of the graft to the coronary artery and the blood supplying artery the surgeon must have relatively unobstructed access to the anastomosis site within the patient. In the less invasive surgical approaches, some of the major coronary arteries including the ascending aorta cannot be easily reached by the surgeon because of their location. This makes hand suturing by keyhole access either difficult or impossible for some coronary artery and aortic sites. In addition, the conditions of some target vessels, such as heavily calcified coronary vessels, vessels having very small diameters, and previously bypassed vessels may make the suturing process difficult or impossible.

Accordingly, it would be desirable to provide a sutureless vascular anastomosis device which easily connects a graft vessel to a target vessel. Sutureless vascular anastomosis devices have been proposed such as those described in U.S. Pat. Nos. 5,234,447; 5,695,504; 6,113,612; and 6,152,937 which allow the connection of the end of a graft vessel to a side of a target vessel without hand suturing. However, performing an anastomosis procedure with these sutureless devices still requires clamping of the target vessel prior to formation of an incision in the target vessel and connection of the graft vessel to the target vessel.

U.S. Pat. No. 6,068,637 describes the combination of an intra vascular catheter, clips, and a cutter used to perform a vascular anastomosis procedure without the need to clamp the target vessel during the anastomosis procedure. However, this system has the drawback that the cutter is inserted through the lumen of the graft vessel. It is highly undesirable to insert any instrument, such as the cutter, through the lumen of a graft vessel because such a procedure causes damage to the endothelial cells lining the graft vessel and associated difficulties.

Accordingly, it would be desirable to provide a sutureless vascular anastomosis device which connects a graft vessel to a target vessel without the need to clamp the target vessel or to pass an instrument through the lumen of the graft vessel.

SUMMARY OF THE INVENTION

The present invention relates to an anastomosis tool for forming an opening in a target vessel and connecting a graft vessel to the target vessel including a tool body, a cutting device movably attached to the tool body and having a distal end configured to form an opening in the target vessel, and a graft vessel attachment device movably attached to tool body and having a distal end configured to connect the graft vessel to the target vessel.

In accordance with one aspect of the present invention, an anastomosis tool for forming an opening in a target vessel and delivering an anastomosis device connecting a graft vessel to the target vessel includes a graft vessel attachment device having a proximal end, a distal end, a lumen extending substantially from the proximal end to the distal end, an axis of the lumen, and an off-axis area extending outward from the lumen at a location between the proximal end and the distal end, and a cutting device slidably disposed within the lumen, the cutting device configured to extend beyond the distal end of the tool body to form an opening in the target vessel and to move into the off-axis area of the tool body after formation of the opening.

In accordance with an additional aspect of the present invention, a device for forming an opening in a target vessel and delivering an implantable anastomosis device to connect a graft vessel to the target vessel includes a tool body having a lumen for delivering an implantable anastomosis device to a target vessel, the lumen having an axis, a graft vessel attachment device movable within the lumen of the tool body for delivering the implantable anastomosis device to the target vessel to connect a graft vessel to the target vessel, and a cutting device for forming an opening in the target vessel substantially along the axis of the tool body, the cutting device being movable within the lumen of the tool body. At least one of the graft vessel attachment device and the cutting device is configured to move transversely out of the lumen.

In accordance with a further aspect of the invention, a device for forming an opening in a target vessel, delivering an implantable anastomosis device to the target vessel, and connecting a graft vessel to a target vessel, includes a cutting device configured to form an opening in the target vessel and a graft vessel attachment device configured to deliver and deploy an implantable anastomosis device to connect the graft vessel and the target vessel. The cutting device and the graft vessel attachment device are provided in an integral tool which does not pass elements through a lumen of the graft vessel.

In accordance with an additional aspect of the present invention, a method of performing anastomosis includes providing an anastomosis tool body having a cutting device and a graft vessel attachment device movable connected by the anastomosis tool body; forming an opening in the wall of a target vessel with the cutting device; moving the cutting device out of the opening in the wall of the target vessel without moving the cutting device through a lumen of the graft vessel; passing the graft vessel attachment device into the opening in the wall of the target vessel; and performing an anastomosis with the graft vessel attachment device.

In accordance with a further aspect of the invention, an anastomosis tool for forming an opening in a target vessel and connecting a graft vessel to the target vessel includes a tool body having an opening at a distal end, a cutting device positioned in the tool body and having a distal end configured to form an opening in the target vessel. The cutting device distal end is movable through the opening in the distal end of the tool body. A graft vessel attachment device is positioned in the tool body and has a distal end configured to connect the graft vessel to the target vessel. At least the distal end of the graft vessel attachment device is movable through the opening in the distal end of the tool body.

In accordance with an additional aspect of the present invention, a device for forming an opening in a target vessel, delivering an implantable anastomosis device to the target vessel, and connecting a graft vessel to a target vessel includes a cutting device configured to form an opening in the target vessel and a graft vessel attachment device configured to deliver and deploy an implantable anastomosis device to connect the graft vessel and the target vessel. The cutting device and the graft vessel attachment device are mechanically linked to sequentially pass the cutting device and the graft vessel attachment device through a predetermined point at an anastomosis site.

BRIEF DESCRIPTION OF THE DRAWING FIGURES

The invention will now be described in greater detail with reference to the alternative embodiments illustrated in the accompanying drawings, in which like elements bear like reference numerals, and wherein.

DETAILED DESCRIPTION OF THE INVENTION

Figure 1:
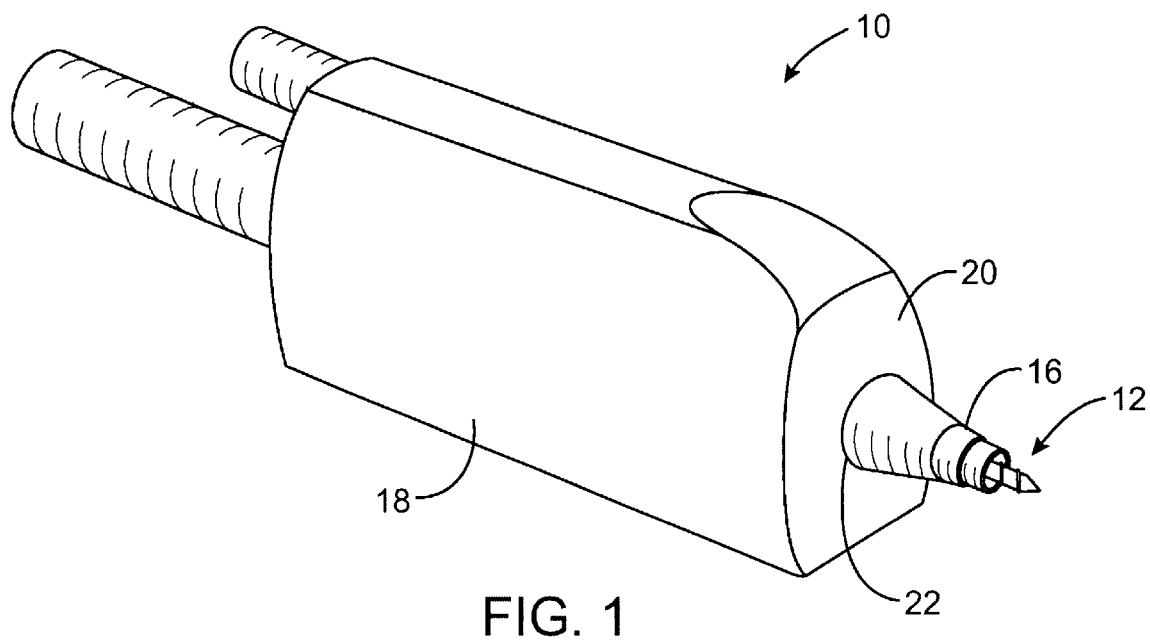
FIG. 1 is a perspective view of an integrated anastomosis tool according to the present invention.
Figure 2:
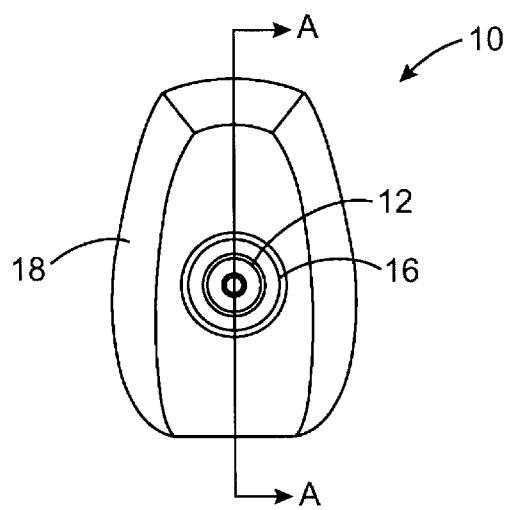
FIG. 2 is a front view of the integrated anastomosis tool of FIG. 1.

FIG. 1 illustrates an integrated anastomosis tool 10 for both creating an opening in a side wall of a target blood vessel and performing an anastomosis procedure to connect a graft vessel to a side of the target blood vessel with a single integrated tool. The integrated anastomosis tool 10 of the present invention, shown in FIGS. 1–6, includes a cutting device 12, a graft vessel attachment device 14, an introducer 16, and a tool body 18. The anastomosis procedure is performed with the integrated anastomosis tool 10 on a pressurized target vessel without the need for clamping of the target vessel. The anastomosis procedure can be performed on a pressurized vessel since there is no need to interchange tools during the procedure.

In each of the embodiments of the present invention, the advancement paths of a cutting device and a graft vessel attachment device cross, intersect, or align so that both the cutting device and the graft vessel attachment device can both be operated by a single tool at the same intended anastomosis site in a sequential manner. The integrated anastomosis tool 10 mechanically links the cutting device and graft vessel attachment device throughout the anastomosis procedure and allows the two devices to be passed sequentially to the anastomosis site. The devices may be separated from the tool after the procedure is complete.

The integrated anastomosis tool 10 allows the use of a single tool for both cutting a hole in a target vessel and attaching a graft vessel to the target vessel by sequentially advancing the cutting device 12 and the graft vessel attachment device 14 within the tool body 18 in one of the methods which will be described with respect to the embodiments illustrated in the figures. In each of the embodiments described herein, the cutting device and graft vessel attachment device are moved to the anastomosis site without passing through the graft vessel. In addition, no parts of elements of the cutting device and graft vessel attachment device pass through the graft vessel preventing possible damage to the graft vessel.

In an off-axis cutting device embodiment, illustrated in FIGS. 1–6, a cutting device is moved off-axis to allow entry of the graft vessel attachment device into the target vessel. In a dual off-axis device, illustrated in FIGS. 7–9, both the cutting device and the graft vessel attachment device are movable off-axis to allow both the cutting device and the graft vessel attachment device to be advanced through a common lumen or opening into the target vessel. In an off-axis graft vessel attachment device embodiment, illustrated in FIGS. 10–12, a cutting device is removed along an axis of the tool while a graft vessel attachment device is advanced from an off-axis position. In Y arrangement embodiments, illustrated in FIGS. 13A and 13B, a cutting device and a graft vessel attachment device are alternately advanced through a pivoting or stationary introducer. Although these specific methods of sequential delivery are illustrated and described, the invention relates to all methods of sequential delivery of a cutting device and graft vessel attachment device with an integrated or mechanically linked tool.

FIG. 1 illustrates the integrated anastomosis tool 10 with the cutting device 12 in an advanced position for cutting an opening in a side wall of a target vessel. The tool body 18 has a distal surface 20 with an opening 22 through which the cutting device 12 is advanced. According to one embodiment, the cutting device 12 is advanced along with the introducer 16 and after formation of an opening in the side wall of the target vessel the introducer is inserted into the opening in the target vessel. The introducer 16 maintains hemostasis during removal of the cutting device 12 and insertion of the graft vessel attachment device 14 by limiting blood loss to blood contained within the tool.

The integrated anastomosis tool 10 illustrated herein has been shown without the advancement mechanisms for advancing and retracting the cutting device 12 and the graft vessel attachment device 14. The advancement mechanisms may be removably connected to the tool 10 or may be incorporated in the tool and may be any of the known advancement mechanisms including mechanical advancing mechanisms such as screws, cams, rods, and the like; pneumatic advancing mechanisms; or any other known advancing mechanisms.

Figure 3:
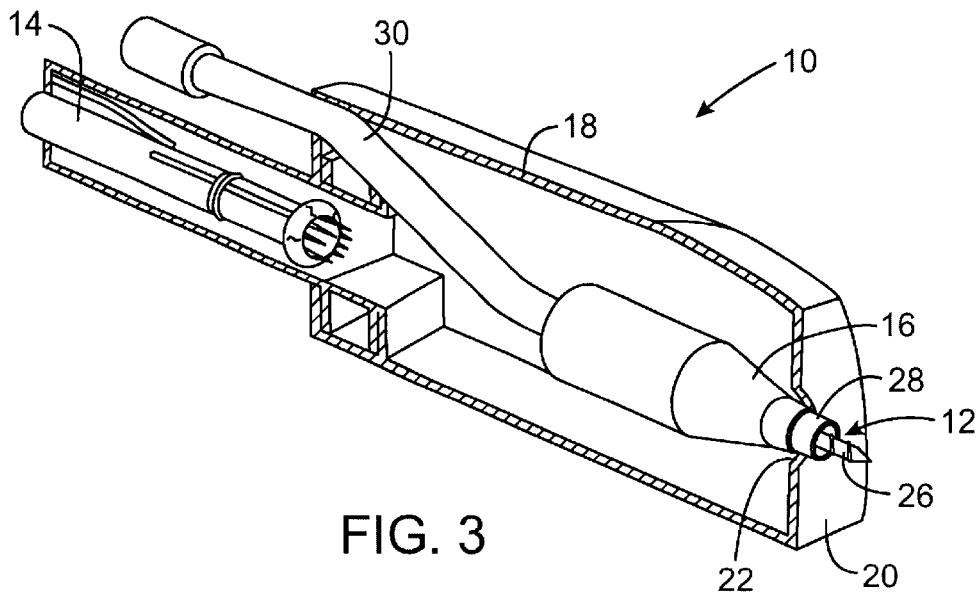
FIG. 3 is a cross sectional perspective view of the integrated anastomosis tool of FIG. 1, taken along line A—A of FIG. 2.
Figure 4:
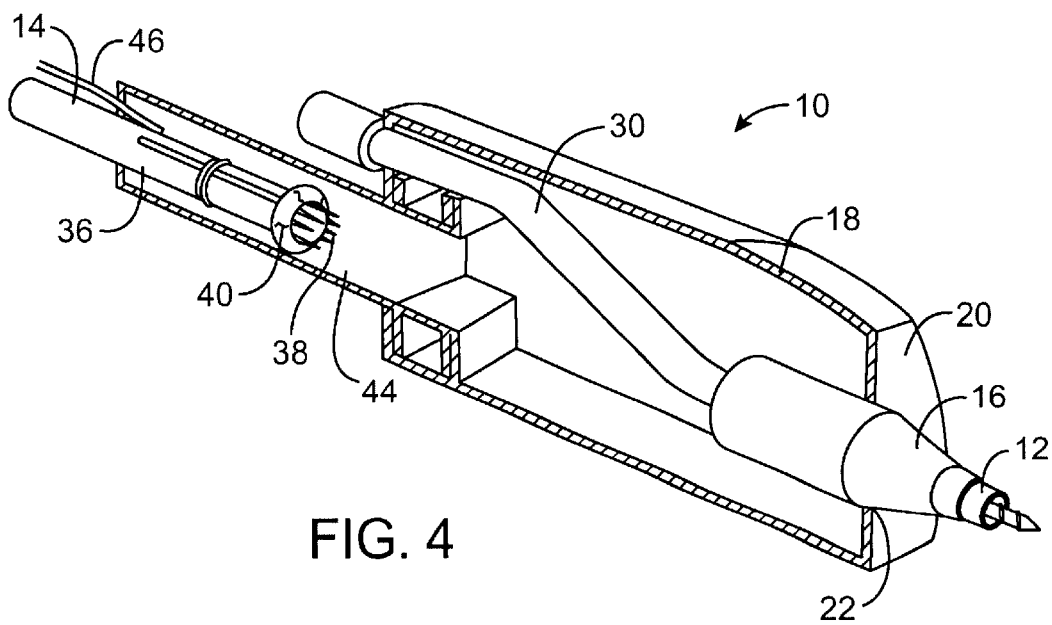
FIG. 4 is a cross sectional perspective view of the integrated anastomosis tool of FIG. 3 with the introducer and punch in an advanced position.

Referring to FIG. 3, one embodiment of a cutting device 12 is shown. The cutting device 12 is partially advanced within the tool body 18 for cutting an opening in the target vessel. In an initial position, prior to deployment, the cutting device 12 may be completely within the tool body 18 or partially extended through the distal opening 22 as shown in FIG. 3. The cutting device 12 includes an auger needle 26 and a circular cutter blade 28. Alternatively, the cutter blade 28 may be a non-circular continuous shape, such as an oval. The cutting device 12 is advanced by simultaneous forward and rotary motion to the fully extended position illustrated in FIG. 4. As the auger needle 26 is advanced and rotated into the target vessel wall, the auger grasps and holds the tissue of the target vessel wall while the circular blade 28 cuts a clean hole or opening in the target vessel wall. The plug of tissue cut by the circular blade 28 is captured on the auger needle 26 for removal with the cutting device 12.

Surrounding the cutting device 12 is the introducer 16 which may be advanced with the cutting device, advanced separately from the cutting device, or held in place. Upon cutting of the opening in the target vessel wall, a distal end of the introducer 16 is advanced into the opening allowing the cutting device 12 to be removed and the graft vessel attachment device to be inserted.

In the embodiment of FIGS. 1–6, the cutting device 12 and the introducer 16 are mounted on a shaft 30 for longitudinal movement within the tool body 18. After advancement of the cutting device 12 and the introducer 16 to the position illustrated in FIG. 4, the introducer is held in place by a locking mechanism (not shown) while the cutting device is retracted.

Figure 5:
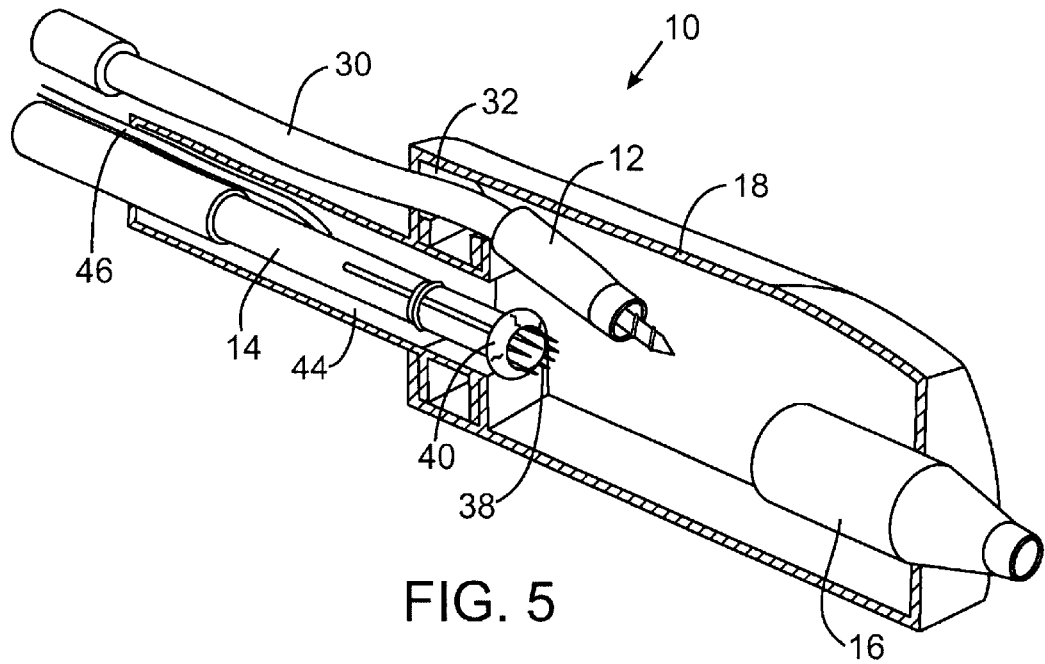
FIG. 5 is a cross sectional perspective view of the integrated anastomosis tool of FIG. 3 with the punch in a partially retracted position.

FIG. 5 illustrates the integrated anastomosis tool 10 with the cutting device 12 being retracted into a storage position. The cutting device is retracted by pulling on the cutter shaft 30. The tool body 18 has a recess 32 which holds the cutting device 12 in place in the storage position.

Once the cutting device 12 has been retracted, a clear path exists for the graft vessel attachment device 14 to be advanced axially through the introducer 16 to perform the anastomosis procedure. This clear path may be referred to as the lumen of the tool and may include the path through the introducer 16. As shown in FIGS. 3–6 the graft vessel attachment device 14 includes a shaft 36, an implantable anastomosis device 38 attached to the shaft, and a graft vessel 40. The graft vessel 40 extends through the shaft 36 and through the implantable device 38. An end of the graft vessel 40 is everted over the end of the implantable device 38.

Figure 6:
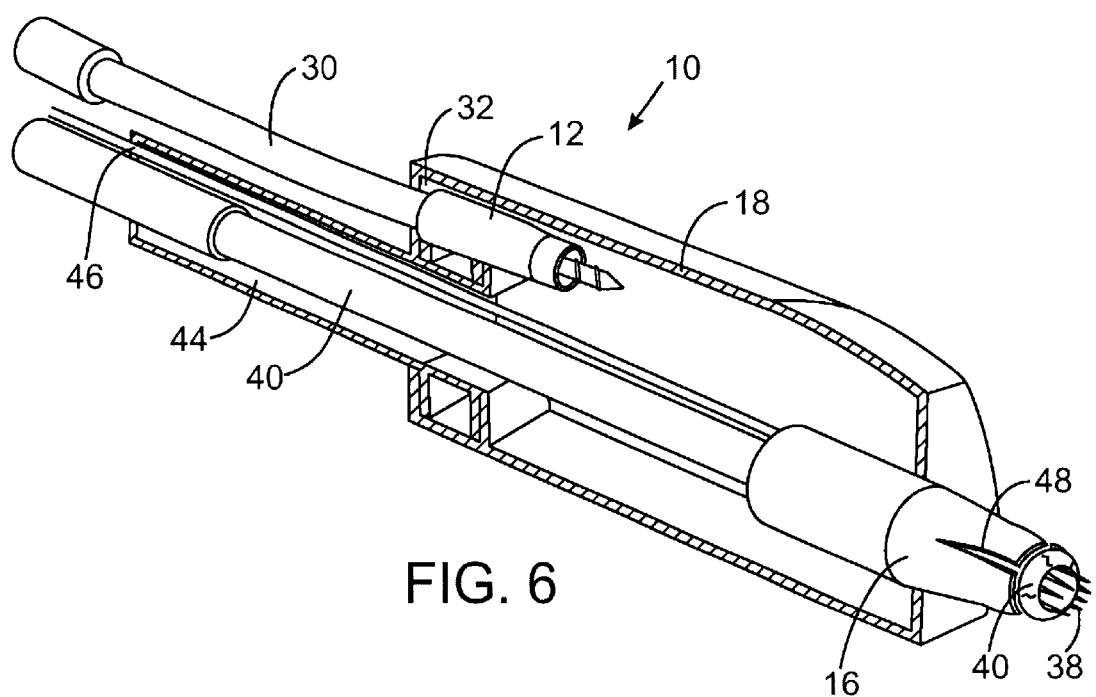
FIG. 6 is a cross sectional perspective view of the integrated anastomosis tool of FIG. 3 with the cutting device in a fully retracted position and the graft vessel attachment device in an advanced position.

During the cutting of the target vessel, the graft vessel attachment device 14 is contained within the tool body 18 in a chamber 44 which is substantially axially aligned with the opening 22. The graft vessel attachment device 14 is advanced by a rod 46, as shown in FIG. 6. The introducer 16 includes a plurality of slits 48 which allow the distal end of the introducer to expand as the implantable device 38 passes through the introducer. In one embodiment, the introducer 16 is a plastic introducer with weakened lines along which the introducer splits upon application of a force.

Upon advancement of the graft vessel attachment device 14, the implantable anastomosis device 38 is deployed in a known manner to connect the end of the graft vessel 40 to the side of the target vessel to achieve blood flow therebetween. After deployment, the integrated anastomosis tool 10 is removed from the graft vessel by sliding the entire tool 10 off of the graft vessel 40.

Figure 7:
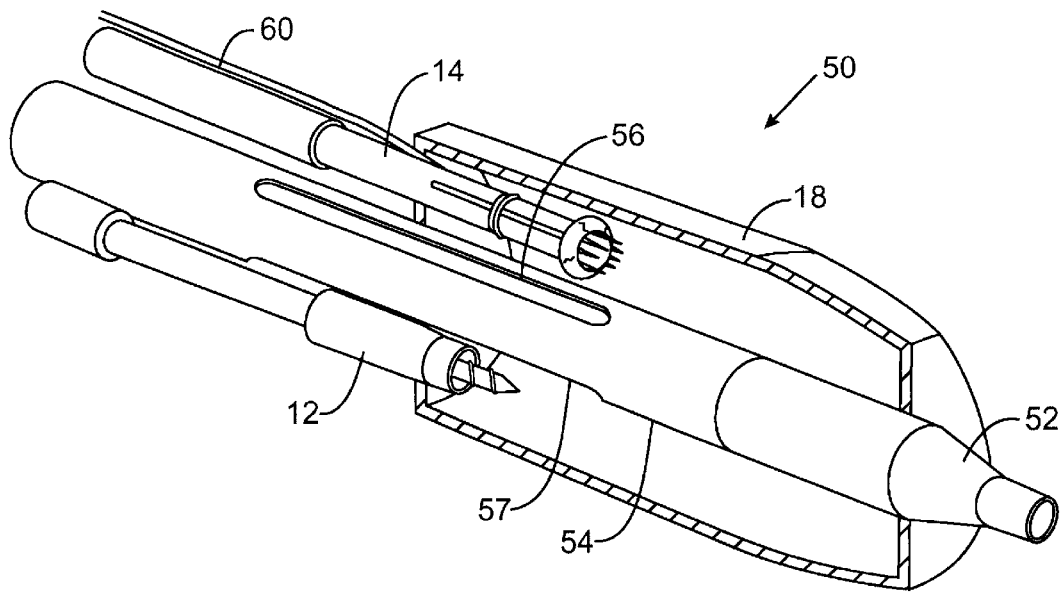
FIG. 7 is a cross sectional perspective view of an alternative embodiment of an integrated anastomosis tool with a cutting device and graft vessel attachment device in retracted positions.
Figure 8:
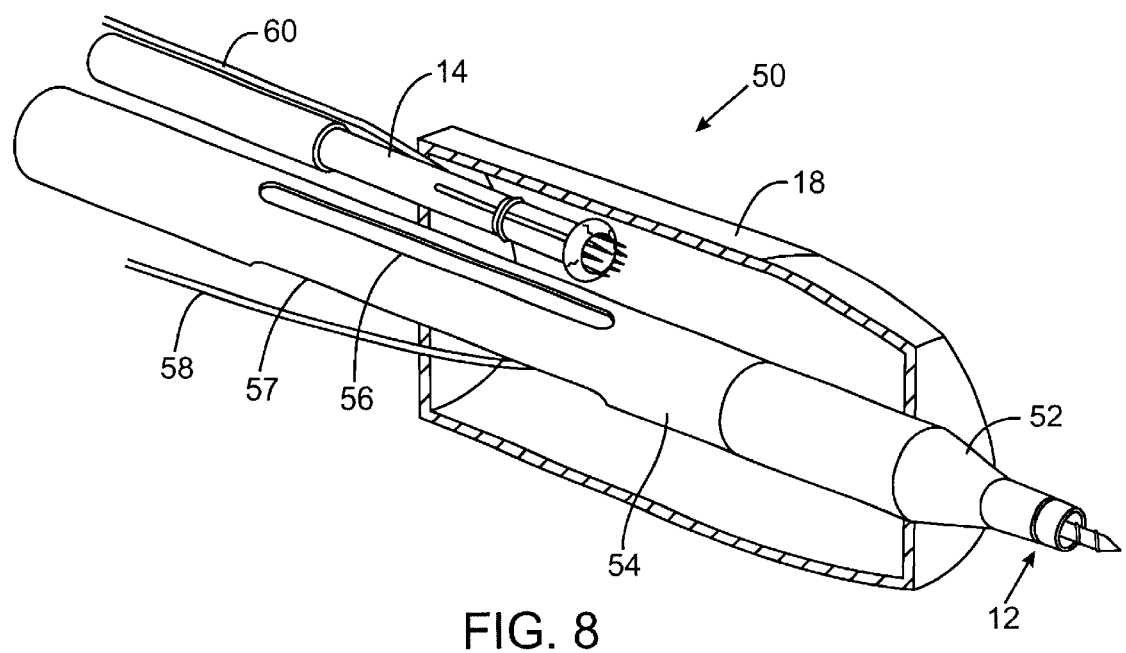
FIG. 8 is a cross sectional perspective view of the integrated anastomosis tool of FIG. 7 with the cutting device in an advanced position.
Figure 9:
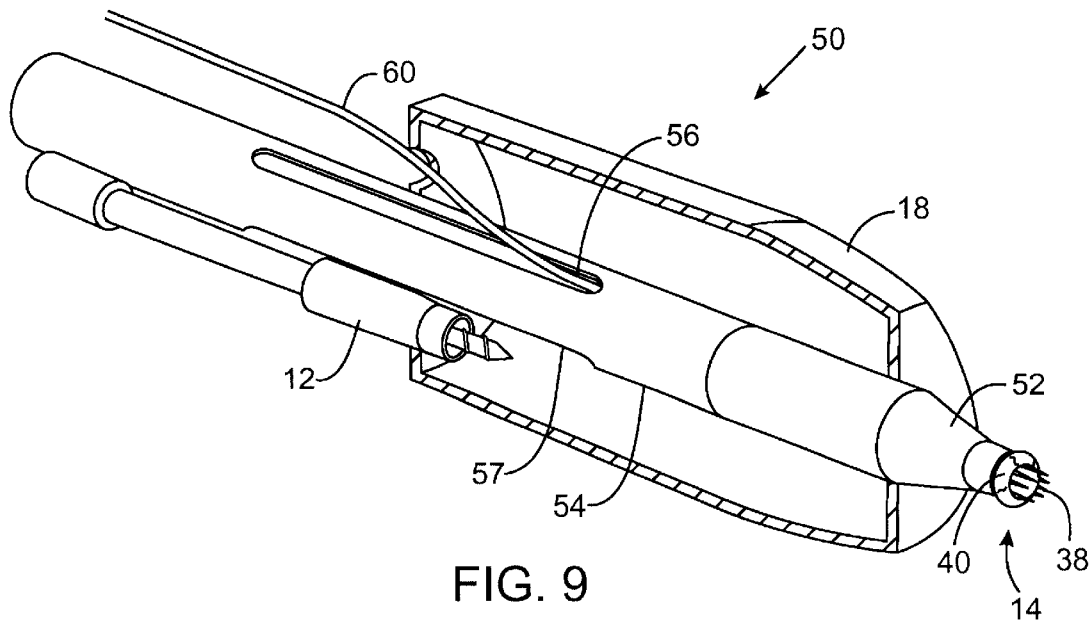
FIG. 9 is a cross sectional perspective view of the integrated anastomosis tool of FIG. 7 with the cutting device in a retracted position and the graft vessel attachment device in an advanced position.

FIGS. 7–9 illustrate an alternative embodiment of an integrated anastomosis tool 50 in which the cutting device 12 and the graft vessel attachment device 14 are sequentially moved transversely into a common channel and advanced to an anastomosis site. As shown in FIG. 7, an introducer 52 is fixed in the tool body 18 and guides the devices to the anastomosis site. Connected to a proximal end of the introducer 52 is a tubular member 54 having two side slits 56, 57 for transversely introducing the cutting device 12 and the graft vessel attachment device 14 into the tubular member. The cutting device 12 is mounted on a first leaf spring 58 and the graft vessel attachment device 14 is mounted on a second leaf spring 60 which are used for advancing and withdrawing these devices.

As shown in FIGS. 8 and 9, the cutting device 12 is first moved transversely into the tubular member 54 through the side slit 57 and then advanced or shuttled through the tubular member 54 and the introducer 52 to cut a plug of tissue in the manner described above. The cutting device 12 is removed from the tubular member 54. A ramp within the tubular member 54 may be used to guide the cutting device out of the side slit 57. The graft vessel attachment device 14 is moved transversely into the tubular member and shuttled forward through the tubular member and the introducer in the same manner. In this way, the two devices are shuttled to and from the anastomosis site through a single introducer 52 from an integral tool body 18.

Figure 10:
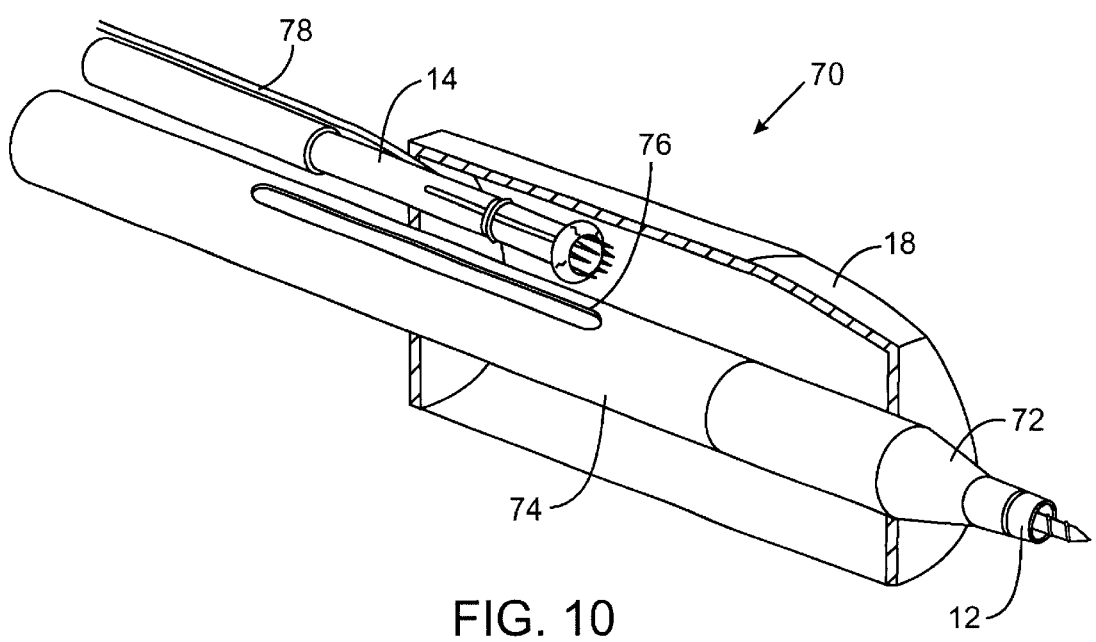
FIG. 10 is a cross sectional perspective view of another embodiment of an integrated anastomosis tool with a side mounted graft vessel attachment device and a cutting device in an advanced position.
Figure 11:
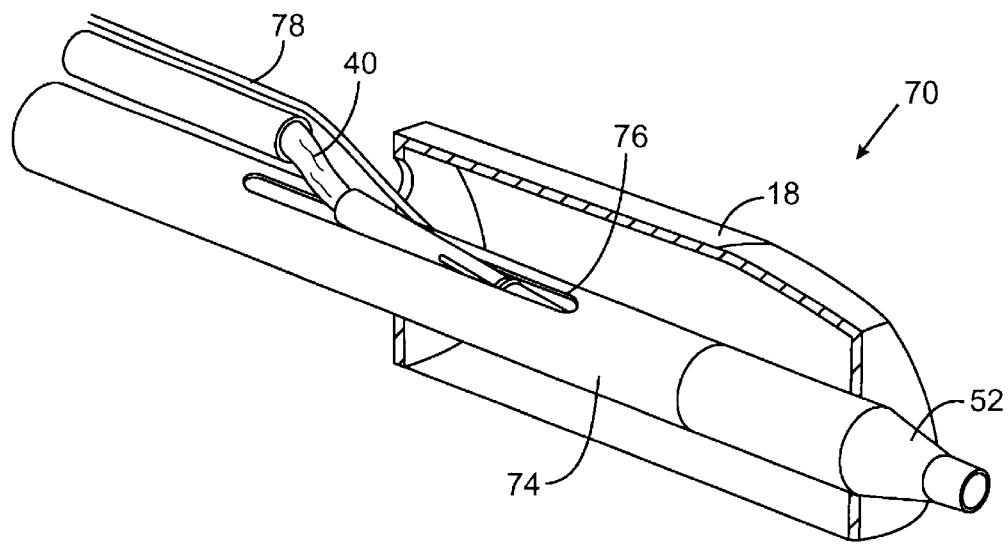
FIG. 11 is a cross sectional perspective view of the integrated anastomosis tool of FIG. 10 with the cutting device in a retracted position and the graft vessel attachment device beginning to be advanced.
Figure 12:
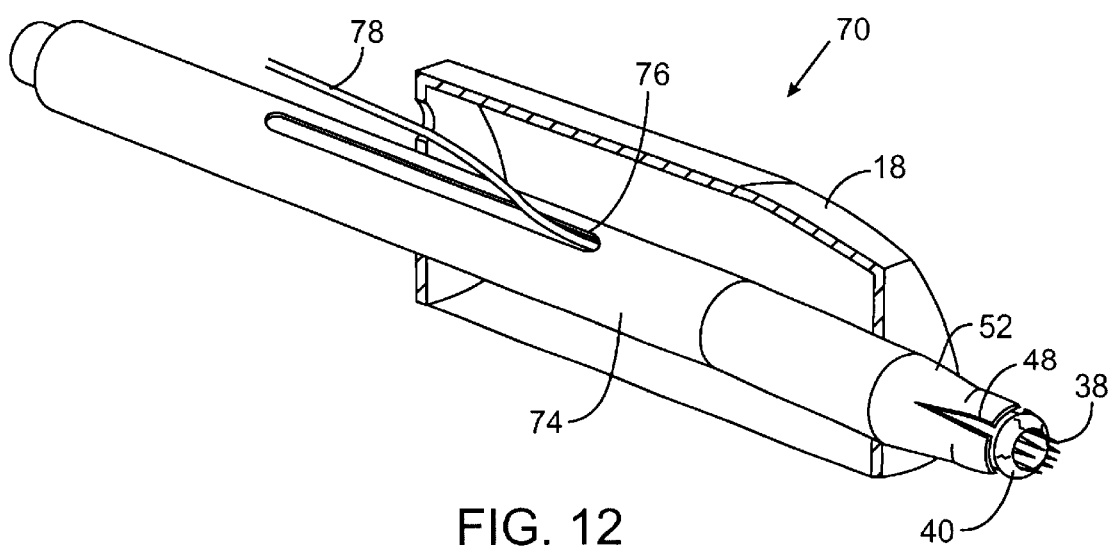
FIG. 12 is a cross sectional perspective view of the integrated anastomosis tool of FIG. 10 with the graft vessel attachment device advanced.

FIGS. 10–12 illustrate an alternative embodiment of an integrated anastomosis tool 70 including a cutting device 12 which is positioned inside a tubular member 74. The cutting device 12 is advanced substantially axially through the tubular member 74 and an introducer 72 to an anastomosis site. A graft vessel attachment device 14 of the integrated anastomosis tool 70 is initially positioned in the tool body 18 beside the tubular member 74. The tubular member 74 has a side slit 76 sized to allow the graft vessel attachment tool 14 to be moved transversely into the tubular member 74. Once the cutting device 12 has been advanced to cut the opening in the target vessel and withdrawn to a position substantially proximal of the slit 76, the graft vessel attachment device 14 is moved transversely into the tubular member 74.

The graft vessel attachment device 14 and/or the cutting device 12 in the embodiments described above may be moved transversely in any known manner. For example, the graft vessel attachment device 14 of FIG. 10 may be mounted on a leaf spring element 78 which permanently biases the graft vessel attachment device toward the tubular member 74. Prior to deployment, the graft vessel attachment device 14 is retained outside the tubular member 74 by any known type of holding mechanism. An initial lack of alignment between the side slit 76 and the graft vessel attachment device 14 can function as a holding mechanism. After the cutting device 12 has been actuated to cut an opening in the target vessel, it is withdrawn. Then the holding mechanism is release or the graft vessel attachment device 14 is aligned with the side slit 76 and the leaf spring element 78 moves the graft vessel attachment device into the lumen of the tubular member 74 due to the bias of the spring. The leaf spring element 78 also functions to advance the graft vessel attachment device 14 through the tubular member 74 and the introducer 72 to the position illustrated in FIG. 12 for deployment of the implantable anastomosis device 38.

Figure 13A:
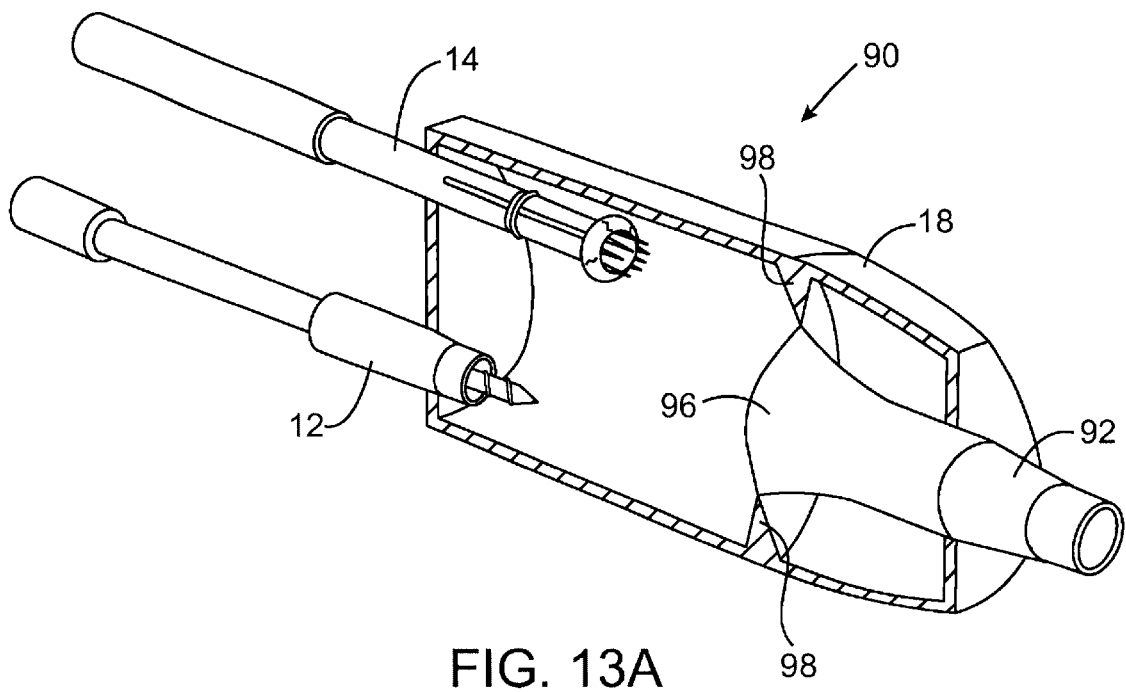
FIG. 13A is a cross sectional perspective view of a further embodiment of an integrated anastomosis tool according to another embodiment of the invention.

FIG. 13A illustrates an alternative embodiment of an integrated anastomosis tool 90 in which the cutting device 12 and the graft vessel attachment device 14 are arranged to be advanced along intersecting paths which form a substantially Y-shape. The integrated tool 90 includes an introducer 92. The tool body 18 also includes two internal deflectors or ramps 98 for directing the cutting device 12 and the graft vessel attachment device 14 along the intersecting paths.

In operation of the integrated anastomosis tool 90 of FIG. 13A, the cutting device 12 is first advanced within the tool body 18 until a distal end of the cutting device 12 contacts the ramp 98 and is directed into a funnel shaped proximal end 96 of the introducer 92.

Figure 13B:
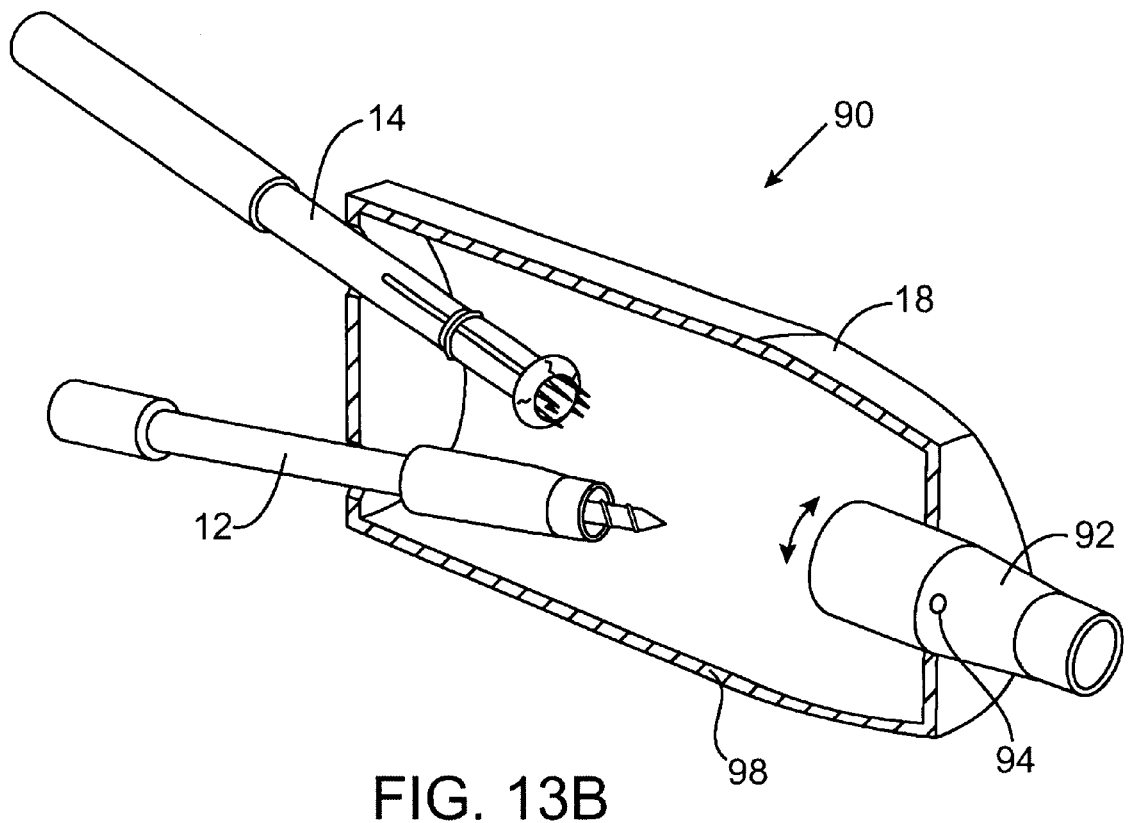
FIG. 13B is a cross sectional perspective view of another embodiment of an integrated anastomosis tool with a pivoting introducer.

FIG. 13B illustrates an alternative embodiment of the integrated anastomosis tool 90 with a Y arrangement and an introducer 92 pivotally mounted in the tool body on two pivots 94. The introducer 92 is pivotable to accommodate the different directions of advancement of the cutting device 12 and the graft vessel attachment tool 14.

In both embodiments of FIGS. 13A and 13B, after cutting the opening in the sidewall of the target vessel with the cutting device 12, a distal end of the introducer 92 is inserted into the opening to prevent blood loss and maintain alignment between the introducer and the opening. The cutting device 12 is then withdrawn to a storage position outside of the introducer 92 for advancement of the graft vessel attachment device 14.

The graft vessel attachment device 14 is advanced distally in the same manner as the cutting device 12 to contact the ramp 98 or enter the pivoting introducer 92 and is directed through the introducer 92. The graft vessel is then attached to the target vessel in any known manner.

Although it is described that the introducers be inserted into the opening in the target vessel in each of the embodiments of the present invention, it is also possible to use the integrated anastomosis tools described herein without inserting an introducer into the opening if the cutting device and graft vessel attachment device are interchanged quickly to minimize blood loss. However, the introducer also provides the advantage of locating the opening in the target vessel for the connection of the graft vessel.

Figure 14:
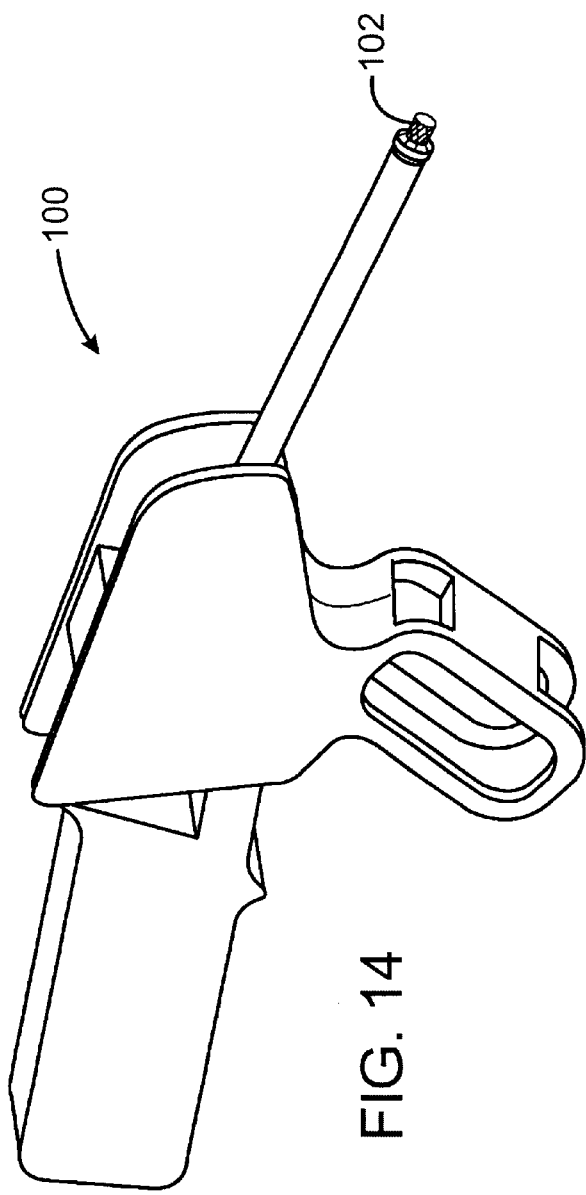
FIG. 14 is a schematic perspective view of one embodiment of a graft vessel attachment device for use in the present invention.
Figure 15:
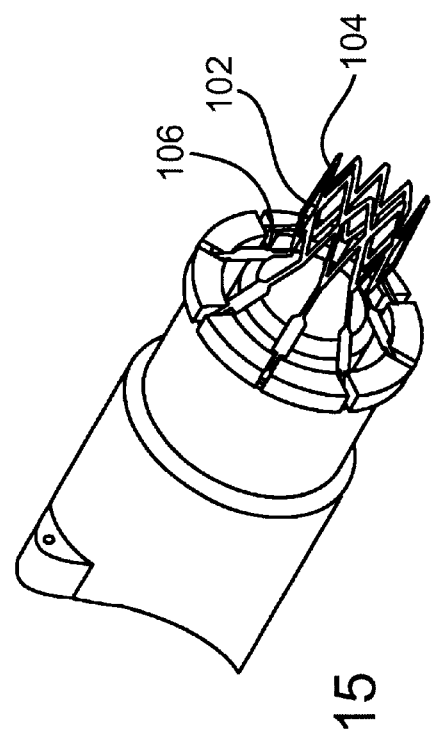
FIG. 15 is an enlarged perspective view of a portion of the graft vessel attachment device of FIG. 14 with an implantable anastomosis device positioned thereon.

FIGS. 14 and 15 illustrate one exemplary embodiment of a graft vessel attachment device 100 which may be incorporated in the integrated tool of the present invention for deploying a one piece implantable anastomosis device 102. The implantable anastomosis device 102 is deployed by the expansion of a distal linkage 104 and a proximal linkage 106 to form distal and proximal flanges which trap the side wall of the target vessel between the flanges. The operation and deployment of this implantable anastomosis device is described in detail in International Application No. WO 00/69343, which is incorporated herein by reference in its entirety.

The graft vessel attachment device 14 for use in the present invention may be any of the known automated anastomosis systems such as those that use staples, sutures, one piece devices, or multi-piece devices to connect an end of a graft vessel to an opening in a side wall of a target vessel. Examples of other graft vessel attachment devices are described in U.S. Pat. Nos. 6,179,849 and 6,206,913, in International Application No. WO 01/08601, and in the references cited therein.

FIGS. 16–21 illustrate one exemplary embodiment of a cutting device 120 for use in the present invention wherein a one piece piercing element 122 is movable within an introducer 124 with a circular cutting edge 126 at a distal end. The piercing element 122 can be retracted by a spring steel strap 128 to a storage position within the introducer 124.

Figure 16:
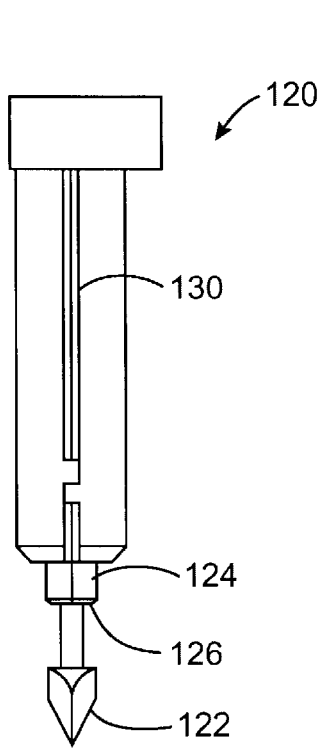
FIG. 16 is a side view of a cutting device having a piercing element in side window through which the piercing element is retractable in accordance with one embodiment of the invention.

As shown in FIG. 16, the introducer 124 is bifurcated along cuts 130 to allow the introducer to expand so that a graft vessel attachment device can pass through the introducer. An elongated opening 132 is located on one side of the introducer 124 between the cuts 130.

Figure 18:
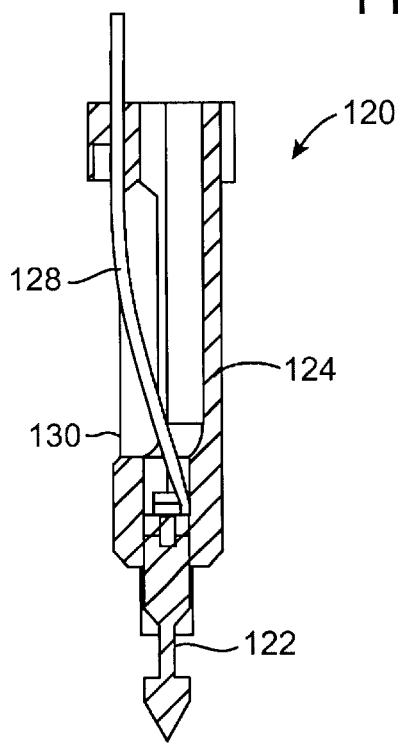
FIG. 18 is a side cross sectional view of the cutting device of FIG. 16, taken along line B—B of FIG. 17.
Figure 19:
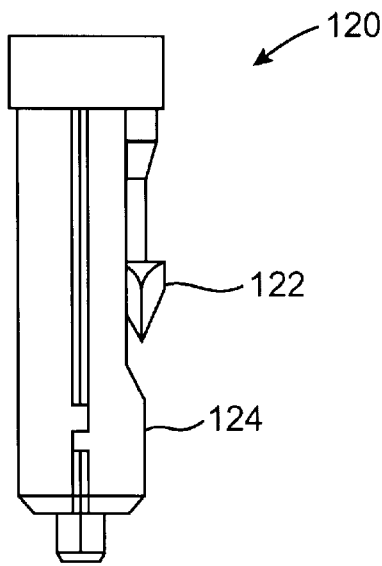
FIG. 19 is a side view of the cutting device of FIG. 16 with the piercing element in a retracted position.
Figure 20:
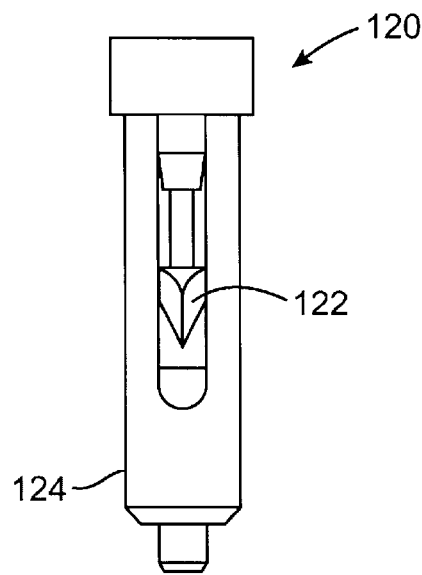
FIG. 20 is a front view of the cutting device of FIG. 16 with the piercing element in the retracted position.
Figure 21:
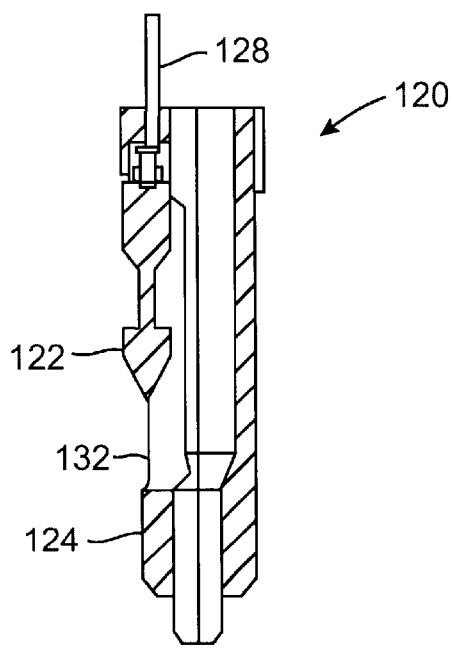
FIG. 21 is a side cross sectional view of the cutting device of FIG. 16 with the piercing element in the retracted position.

As shown in FIGS. 19–21, the piercing element 122 can be retracted into the introducer 124 by a member such as spring steel strap or cable 128 which extends out of the opening 132. The piercing element 122 is slidable in a bore in the introducer 124 from an incision forming position outside the introducer (FIGS. 13–18) to a storage position in the opening 132 (FIGS. 19–21). With this arrangement, the strap 128 holds the piercing element 122 in the forward position when it is pierced through the target vessel wall (e.g., aorta wall) and the piercing element can then be pulled to the storage position by pulling back on the strap. With the piercing element thus pulled out of the opening 132, an anastomosis device can be delivered through the bore in the introducer 124 to the incision site. Because the two halves of the introducer 124 can be separated to allow radial expansion of the introducer, the implantable anastomosis device and the deployment device for delivering the implantable device can be larger than the bore in the introducer.

Figure 17:
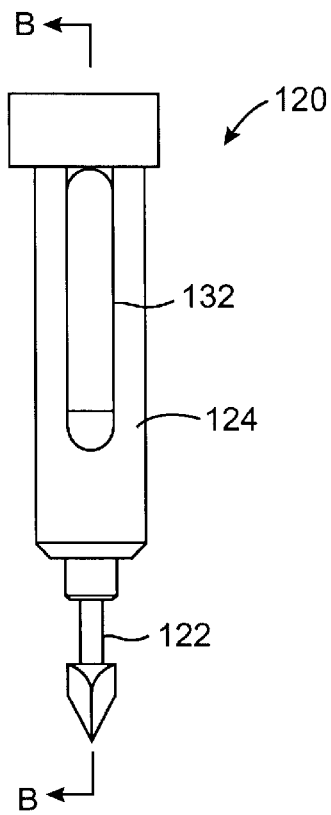
FIG. 17 is a front view of the cutting device of FIG. 16.

The term "cutting device," as used herein, is intended to mean any instrument which forms an opening in a target vessel, including tissue punches which cut a plug of tissue as shown in FIGS. 16–18, rotatable tissue cutters as shown in FIGS. 1–15, and all other tissue cutters and punches which form an incision or opening in a target vessel. The motion of the cutting device 12 relative to the tool body 18, as described above, is independent of the particular embodiment of the cutting device 12 that is utilized.

While the invention has been described in detail with reference to the alterative embodiments thereof, it will be apparent to one skilled in the art that various changes and modifications can be made and equivalents employed, without departing from the present invention.

What is claimed is:

1. An integrated anastomosis tool for forming an opening in a target vessel and connecting a graft vessel to the target vessel, the device comprising:
    a tool body;
    a cutting device movably attached to the tool body and having a distal end configured to form an opening in the target vessel; and
    a graft vessel attachment device movably attached to the tool body and having a distal end configured to connect the graft vessel to the target vessel, while substantially sealing against the target vessel;
    wherein the graft vessel attachment device is movable substantially along a first direction and the cutting device is movable both transverse to the first direction and substantially along the first direction.

2. The tool of claim 1, further comprising:
    an implantable anastomosis device operatively coupled to the graft vessel attachment device.

3. The tool of claim 1, wherein the cutting device is a tissue punch.

4. The tool of claim 1, wherein the cutting device includes a circular cutting element.

5. The tool of claim 1, wherein both the graft vessel attachment device and the cutting device are movable along a first direction and movable transverse to the first direction.

6. The tool of claim 1, wherein both the graft vessel attachment device and the cutting device are contained within the tool body simultaneously.

7. An integrated anastomosis tool for forming an opening in a target vessel and connecting a graft vessel to the target vessel, the device comprising:
    a tool body;
    a cutting device movably attached to the tool body and having a distal end configured to form an opening in the target vessel; and
    a graft vessel attachment device movably attached to the tool body and having a distal end configured to connect the graft vessel to the target vessel, while substantially sealing against the target vessel;
    wherein the cutting device is movable along a first direction and the graft vessel attachment device is movable along a second direction non-parallel to the first direction.

8. An integrated anastomosis tool for forming an opening in a target vessel and connecting a graft vessel to the target vessel, the device comprising:
    a tool body;
    a cutting device movably attached to the tool body and having a distal end configured to form an opening in the target vessel; and
    a graft vessel attachment device movably attached to the tool body and having a distal end configured to connect the graft vessel to the target vessel, while substantially sealing against the target vessel;
    wherein the cutting device is movable substantially along a first direction and the graft vessel attachment device is movable both transverse to the first direction and substantially along the first direction.

9. An anastomosis tool for forming an opening in a target vessel and delivering an anastomosis device connecting a graft vessel to the target vessel, the device comprising:
    a graft vessel attachment device having a proximal end, a distal end, a lumen extending substantially from the proximal end to the distal end, an axis of the lumen, and an off-axis area extending outward from the lumen at a location between the proximal end and the distal end; and
    a cutting device slidably disposed at least partially within the lumen, the cutting device configured to extend beyond the distal end of the tool body to form an opening in the target vessel and to move into the off-axis area of the tool body after formation of the opening.

10. The tool of claim 9, further comprising:
    an implantable anastomosis device operatively coupled to the graft vessel attachment device.

11. The tool of claim 10, wherein the implantable anastomosis device is movable through the lumen when the cutting device is moved into the off-axis area.

12. The tool of claim 9, wherein the cutting device is a rotatable cutter.

13. The tool of claim 9, further comprising a spring member connected to the cutting device for moving the cutting device from the lumen of the tool into the off-axis area.

14. The tool of claim 9, wherein the cutting device is configured to move through a side opening to a storage position in the off-axis area in the tool.

15. The tool of claim 9, wherein the cutting device includes a circular cutting element.

16. A device for forming an opening in a target vessel, delivering an implantable anastomosis device to the target vessel, and connecting a graft vessel to a target vessel, the device comprising a cutting device configured to form an opening in the target vessel and a graft vessel attachment device configured to deliver and deploy an implantable anastomosis device to connect the graft vessel and the target vessel, the cutting device and the graft vessel attachment device being provided in an integral tool which does not pass elements through a lumen of the graft vessel.

17. The device of claim 16, wherein the cutting device is configured such that the cutting device is not separated from the graft vessel attachment device after forming the opening in the target vessel.

18. The device of claim 16, wherein the cutting device includes a circular cutting element for cutting a plug of tissue.

19. The device of claim 16, wherein the cutting device and the graft vessel attachment device are configured to move sequentially through a single opening in a distal end of the device.

20. The device of claim 19, wherein the cutting device moves along a first path and the graft vessel attachment device moves along a second path, the first and second paths intersecting substantially at an anastomosis site.

21. A method of performing anastomosis comprising:
providing an anastomosis tool body having a cutting device and a graft vessel attachment device movably connected to the anastomosis tool body;
forming an opening in the wall of a target vessel with the cutting device;
moving the cutting device out of the opening in the wall of the target vessel without moving the cutting device through a lumen of the graft vessel;
passing the graft vessel attachment device into the opening in the wall of the target vessel; and
performing an anastomosis with the graft vessel attachment device.

22. The method of claim 21, wherein the step of moving the cutter device out of the opening in the target vessel includes storing the cutting device at a storage position in the anastomosis tool body.

23. The method of claim 21, wherein the step of moving the cutting device out of the opening in the target vessel includes moving the cutting device transversely with respect to an insertion path of the cutting device.

24. The method of claim 21, wherein the step of forming an opening in the wall of the target vessel with the cutting device includes punching the tissue of the wall of the target vessel.

25. The method of claim 21, wherein the step of forming an opening in the wall of the target vessel with the cutting device includes cutting a plug of tissue with a circular cutting blade.

26. The method of claim 21, wherein the step of forming an opening in the wall of the target vessel with the cutting device includes advancing the cutting device and an introducer into the target vessel, and retaining the introducer in the opening in the target vessel while the cutting device is moved out of the opening in the target vessel.

27. The method of claim 26, wherein the graft vessel attachment device is passed into the opening in the wall of the target vessel through the introducer.

28. The method of claim 26, wherein the introducer provides hemostasis when retained in the opening.

29. The method of claim 26, wherein the introducer and cutting device enter the target vessel substantially simultaneously.

\* \* \* \* \*